United States Patent [19]

Karrer

[11] Patent Number: 4,532,279
[45] Date of Patent: Jul. 30, 1985

[54] POLYALKYLPIPERIDINE ESTERS OF ALIPHATIC TETRACARBOXYLIC ACIDS

[75] Inventor: Friedrich Karrer, Zofingen, Switzerland

[73] Assignee: Ciba-Geigy Corporation, Ardsley, N.Y.

[21] Appl. No.: 571,980

[22] Filed: Jan. 19, 1984

[30] Foreign Application Priority Data

Jan. 31, 1983 [CH] Switzerland .................. 535/83

[51] Int. Cl.$^3$ .............................................. C08K 5/34
[52] U.S. Cl. .................................... 524/102; 546/188; 546/189
[58] Field of Search ................. 524/102; 546/188, 189

[56] References Cited

U.S. PATENT DOCUMENTS

| | | | |
|---|---|---|---|
| 4,136,081 | 1/1979 | Minagawa et al. | 546/188 |
| 4,284,485 | 8/1981 | Berner | 524/102 |
| 4,419,472 | 12/1983 | Berner et al. | 524/102 |
| 4,426,471 | 1/1984 | Berner | 524/102 |

FOREIGN PATENT DOCUMENTS 23330 7/1981 European Pat. Off. .

Primary Examiner—John Kight
Assistant Examiner—Kriellion Morgan
Attorney, Agent, or Firm—Harry Falber

[57] ABSTRACT

Compounds of the formula I

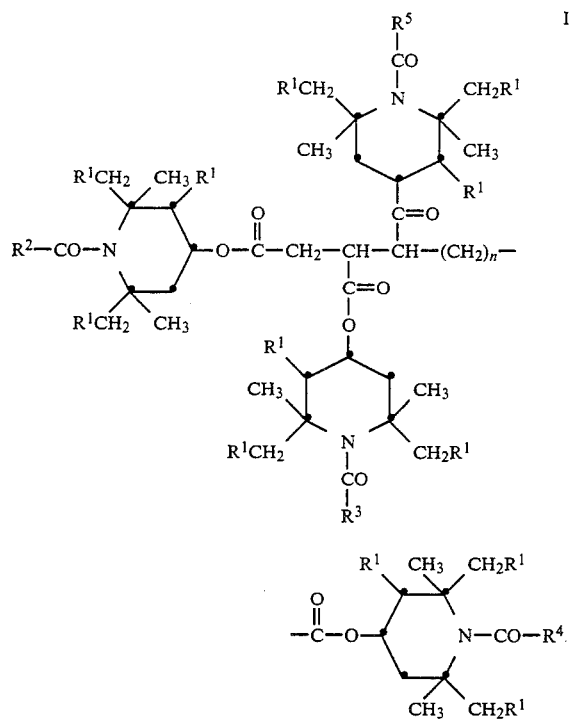

wherein n is 0 or 1, $R^1$ is hydrogen or $C_2$-$C_4$ alkyl, and $R^2$, $R^3$, $R^4$ and $R^5$ are monovalent hydrocarbon radicals, are effective light stabilizers for organic polymers, especially for surface-coating resins.

6 Claims, No Drawings

POLYALKYLPIPERIDINE ESTERS OF ALIPHATIC TETRACARBOXYLIC ACIDS

The present invention relates to novel polyalkylpiperidine esters of aliphatic tetracarboxylic acids, in particular of propane-1,1,2,3- and butane-1,2,3,4-tetracarboxylic acids, and to the use thereof as stabilisers for organic polymers.

Polyalkylpiperidine esters of aliphatic tetracarboxylic acids have been proposed as stabilisers for organic polymers in U.S. Pat. No. 4,136,081. The piperidine groups contained in these compounds have the general formula

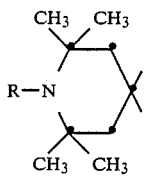

wherein R is hydrogen or O•. These tetra-esters are effective stabilisers for organic polymers, in particular for protecting them against light-induced degradation. Examples of such polymers are polyolefins, styrene polymers, polyvinyl chloride or polyamides. However, those compounds in which R is O• are red in colour and, when used in polymers, result in discoloration of the substrate. The compounds in which R is hydrogen are basic compounds and for this reason are unsuitable for specific utilities. Thus, for example, salt formation may occur with fatty acids which are added to the polymers as lubricants. Complexes can result with heavy metal compounds which are added to certain polymers as stabilisers. However, the basicity of the above mentioned compounds is especially disadvantageous when they are used in acid-catalysed lacquers. In this case, the acid catalyst may precipitate and also insufficient curing of the lacquers may result. It has now been found that these drawbacks do not arise by using esters in which the piperidine nitrogen atoms are substituted by acyl groups. Such compounds have not been known up to now. In particular, the invention relates to the corresponding esters of propane-1,1,2,3- and butane-1,2,3,4-tetracarboxylic acid.

Accordingly, the present invention provides compounds of the formula I

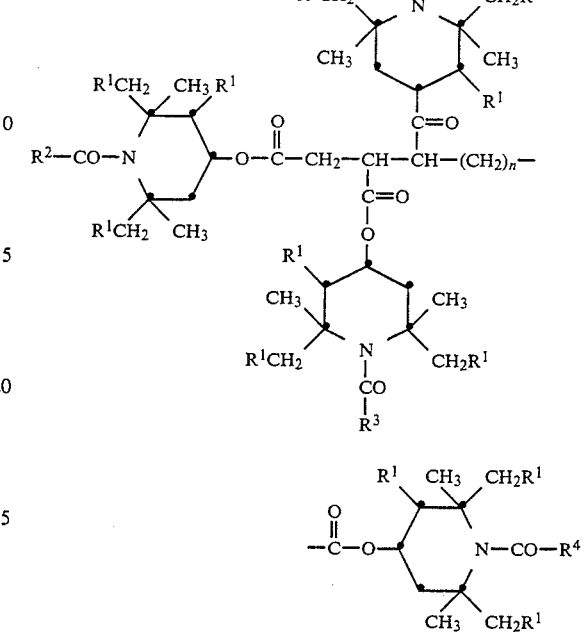

wherein n is 0 or 1, $R^1$ is hydrogen or $C_1$–$C_4$alkyl, and $R^2$, $R^3$, $R^4$ and $R^5$ are each independently hydrogen, $C_1$–$C_{17}$alkyl, $C_2$–$C_{17}$alkenyl, $C_5$–$C_8$cycloalkyl, $C_5$–$C_8$cycloalkylalkyl or $C_5$–$C_8$alkylcycloalkyl, $C_6$–$C_{10}$aryl, $C_7$–$C_{16}$alkylphenyl, $C_7$–$C_{12}$aralkyl or $C_8$–$C_{18}$alkylphenylalkyl.

$R^1$ as $C_1$–$C_4$alkyl may be e.g. methyl, ethyl, propyl or butyl. $R^2$, $R^3$, $R^4$ and $R^5$ as $C_1$–$C_{18}$alkyl may be unbranched or branched alkyl, e.g. methyl, ethyl, isopropyl, n-butyl, sec-butyl, n-pentyl, n-hexyl, 2-ethylbutyl, n-heptyl, n-nonyl, n-undecyl, n-tridecyl, n-tetradecyl or n-heptadecyl.

$R^2$ to $R^5$ as $C_2$–$C_{17}$alkenyl may be e.g. vinyl, 1-methylvinyl, 2-methylvinyl, allyl, 2,2-dimethylvinyl, 3-methyl-2-butenyl, 9-decenyl or 8-heptadecenyl.

$R^2$ to $R^5$ as cycloalkyl, cycloalkylalkyl or alkylcycloalkyl may be e.g. cyclopentyl, cyclohexyl, 4-methylcyclohexyl, 2,4-dimethylcyclohexyl, cyclohexylmethyl or cyclooctyl. $R^2$ to $R^5$ as aryl or alkylphenyl may be e.g. phenyl, naphthyl, 3-methylphenyl, 4-tert-butylphenyl, 3,5-dimethylphenyl or 4-nonylphenyl. $R^2$ to $R^5$ as aralkyl or alkylphenylalkyl may be e.g. benzyl, 2-phenylethyl, 1-phenylethyl, 3-phenylpropyl, 2-naphthylmethyl, 4-methylbenzyl or 4-isopropylbenzyl.

Preferred compounds of the formula I are those in which $R^1$ is hydrogen.

Also preferred are compounds of the formula I, wherein $R^1$ is hydrogen and $R^2$, $R^3$, $R^4$ and $R^5$ are identical and are $C_1$–$C_5$alkyl or $C_2$–$C_5$alkenyl, preferably methyl or vinyl.

Examples of individual compounds of the formula I are:

tetra(1-acetyl-2,2,6,6-tetramethyl-4-piperidyl) propane-1,1,2,3-tetracarboxylate, tetra(1-butyroyl-2,2,6,6-tetramethyl-4-piperidyl) propane-1,1,2,3-tetracarboxylate, 1,1-bis(1-acryloyl-2,2,6,6-tetramethyl-4-piperidyloxycarbonyl)-2,3-bis(1-acetyl-2,2,6,6-tetramethyl-4-piperidyloxycarbonyl)propane,
tetra(1-acetyl-2,2,6,6-tetramethyl-4-piperidyl) butane-1,2,3,4-tetracarboxylate,
tetra(1-propionyl-2,2,6,6-tetramethyl-4-piperidyl) butane-1,2,3,4-tetracarboxylate,
tetra(1-acryloyl-2,2,6,6-tetramethyl-4-piperidyl) butane-1,2,3,4-tetracarboxylate,
tetra(1-phenylacetyl-2,2,6,6-tetramethyl-4-piperidyl) butane-1,2,3,4tetracarboxylate,
tetra(1-methacryloyl-2,2,6,6-tetramethyl-4-piperidyl) butane-1,2,3,4tetracarboxylate,
tetra(1-benzoyl-2,2,6,6-tetramethyl-4-piperidyl) butane-1,2,3,4-tetracarboxylate.
tetra(1-acetyl-2,6-diethyl-2,3,6-trimethyl-4-piperidyl) butane-1,2,3,4-tetracarboxylate.

The compounds of the formula I, wherein $R^2$, $R^3$, $R^4$ and $R^5$ are identical, can be prepared by transesterifying lower alkyl esters of the propane- or butanecarboxylic acid (II) with a 1-acylpolyalkylpiperidin-4-ol (III):

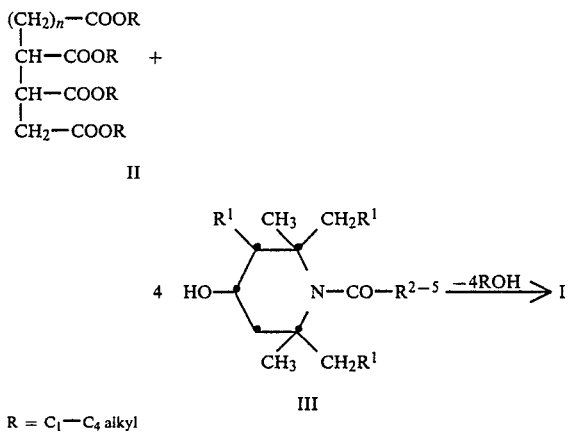

$R = C_1-C_4$ alkyl

In the above process, at least 4 moles of III are reacted with 1 mole of II. The reaction is normally carried out in the presence of a transesterification catalyst. Examples of transesterification catalysts are alkali metals, alkali metal amides, alkali metal hydrides, alkali metal alkoxides, tetraalkyltitanates or organotin compounds, and are e.g. Na, K, $LiNH_2$, $NaNH_2$, NaH, $NaOC_2H_5$, $NaOCH_3$, LiH, KO-tert-$C_4H_9$, $Ti(OC_4H_9)_4$ or dibutyltin oxide. When using such a catalyst the reaction proceeds in the temperature range from 80° to 180° C., preferably from 120°-160° C. The alcohol ROH formed during the reaction is continuously distilled off. If a solvent is used, it will be a high-boiling non-polar solvent, e.g. toluene, xylene, decalin, tetralin or a higher boiling petroleum distillate fraction. However, the transesterification can also be carried out without a solvent.

If a mixture of 2 or more piperidinols (which differ from each other in the acyl radical) are used in this process instead of a single piperidinol III, compounds of the formula I having different acyl radicals are obtained. A mixture of compounds of the formula I is also often obtained. This can be of interest however it is desired to prepare liquid products or products with a low melting point. The properties of the products can be varied by the number and the molar ratio of the different piperidinols.

A second preparatory process comprises transesterifying the tetraester II with a piperidinol IV which is unsubstituted at the nitrogen, and subsequently acylating the resulant piperidyl ester V:

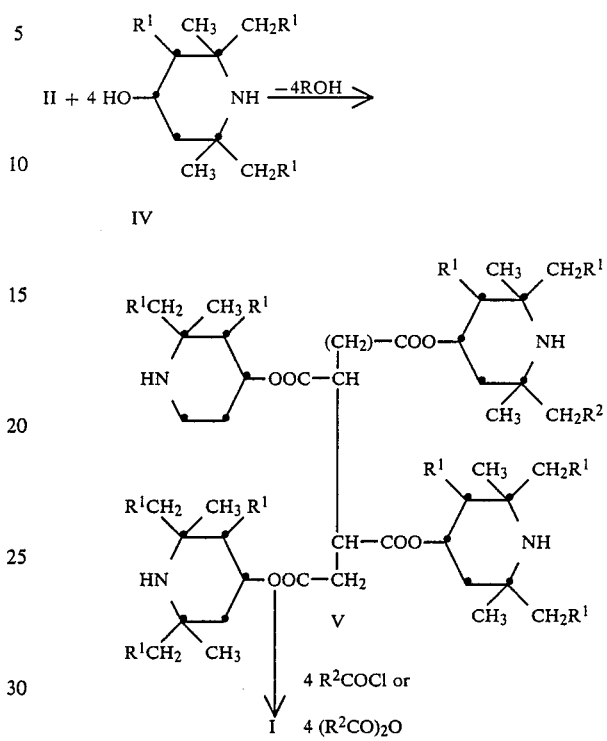

The first step of this reaction corresponds to the transesterification process illustrated above. In the second step, the acylation is carried out with at least 4 moles of carboxylic acid chloride or carboxylic acid anhydride. It is preferred to use an excess of acylating agent. The reaction with carboxylic acid chloride proceeds at room temperature or at lower temperature, and can be speeded up by addition of molar amounts of a base, preferably of a tertiary amine such as triethylamine, tributylamine, pyridine or dimethylaniline, which base acts as HCl acceptor. It is preferred to carry out the process in an inert solvent, e.g. in a hydrocarbon, chlorinated hydrocarbon or an ether.

If a carboxylic acid anhydride is used as acylating agent, the process is preferably carried out in the temperature range from 60° to 100° C. A tertiary amine may be used as catalyst, e.g. dimethylaminopyridine or N-(pyrid-4-yl)pyrrolidine. To introduce the formyl radical it is possible to use a mixed anhydride, e.g. acetylformyl anhydride.

A variant of the two processes comprises carrying out a direct esterification of a tetracarboxylic acid VI

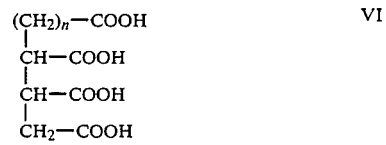

with a piperidinol III or IV instead of the transesterification. In this reaction an acid catalyst is used, e.g. toluenesulfonic acid or phosphoric acid, and the water of reaction is distilled off direct or as an azeotrope.

The compounds of formula I can be used as stabilisers for light-sensitive organic materials, e.g. for cosmetics or colour photographic layers, and especially for organic polymers. In addition to pronounced light stabilising properties, the compounds of formula I also have a certain stabilising action against the thermal and oxidative ageing of polymers. Examples of such polymers are:

1. Polymers of mono- and diolefins, for example polyethylene (which may be crosslinked), polypropylene, polyisobutylene, polybut-1-ene, polymethylpent-1-ene, polyisoprene or polybutadiene, and polymers of cycloolefins, e.g. of cyclopentene or norbornene.

2. Mixtures of the polymers mentioned under (1), for example mixtures of polypropylene with polyethylene or with polyisobutylene.

3. Copolymers of mono- and diolefins with each other or with other vinyl monomers, for example ethylene/propylene copolymers, propylene/butene copolymers, propylene/isobutylene copolymers, ethylene/but-1-ene copolymers, propylene/butadiene copolymers, isobutylene/isoprene copolymers, ethylene/alkylacrylate copolymers, ethylene/alkylmethacrylate copolymers, ethylene/vinyl acetate copolymers, or ethylene/acrylic acid copolymers and salts thereof (isomers), and also terpolymers of ethylene with propylene and a diene, such as hexadiene, dicyclopentadiene or ethylidene norbornene.

4. Polystyrene.

5. Copolymers of styrene or α-methylstyrene with dienes or acrylic derivatives, for example styrene/butadiene, styrene/acrylonitrile, styrene/alkylmethacrylate, styrene/acrylonitrile/methyl acrylate, mixtures of high impact strength obtained from styrene copolymers and another polymer, for example a polyacrylate, a diene polymer or an ethylene/propylene/diene terpolymer; and also block copolymers of styrene, for example styrene/butadiene/styrene, styrene/isoprene/styrene, styrene/ethylene-butylene/styrene, or styrene-ethylene/propylene-styrene.

6. Graft copolymers of styrene, e.g. styrene with polybutadiene, styrene and acrylonitrile with polybutadiene, styrene and maleic anhydride with polybutadiene, styrene and alkyl acrylates or alkyl methacrylates with polybutadiene, styrene and acrylonitrile with ethylene-propylene-diene terpolymers, styrene and acrylonitrile with polyalkylacrylates or polyalkylmethacrylates, styrene and acrylonitrile with acrylate-butadiene copolymers, and mixtures thereof with the copolymers listed under (5), known e.g. as ABS, MBS, ASA or AES polymers.

7. Halogen-containing polymers, e.g. polychloroprene, chlorinated rubber, chlorinated or chlorosulfonated polyethylene, especially polymers of halogenated vinyl compounds, e.g. polyvinyl chloride, polyvinylidene chloride, polyvinyl fluoride, polyvinylidene fluoride, and their copolymers such as vinyl chloride/vinylidene chloride, vinyl chloride/vinyl acetate or vinylidene chloride/vinyl acetate polymers.

8. Polymers which are derived from α,β-unsaturated acids and their derivative, such as polyacrylates and polymethacrylates, polyacrylamides and polyacrylonitriles.

9. Copolymers of the monomers listed in (8) with one another or with other unsaturated monomers, e.g. acrylonitrile/butadiene copolymers, acrylonitrile/alkyl acrylate copolymers, acrylonitrile/vinyl chloride copolymers, or acrylonitrile/alkyl methacrylate/butadiene terpolymers.

10. Polymers which are derived from unsaturated alcohols and amines or their acyl derivatives or acetals, such as polyvinyl alcohol, polyvinyl acetate, polyvinyl stearate, polyvinyl benzoate, polyvinyl maleate, polyvinylbutyral, polyallyl phthalate, polyallyl melamine.

11. Homopolymers and copolymers of cyclic ethers sucsh as polyethylene glycols, polyethylene oxide, polypropylene oxide or their copolymers with bis-glycidyl ethers.

12. Polyacetals such as polyoxymethylene, and also those polyoxymethylenes which contain a comonomer, e.g. ethylene oxide.

13. Polyphenylene oxides and sulfides.

14. Polyurethanes which are derived on the one hand from polyethers, polyesters and polybutadienes containing hydroxy end groups, and from aliphatic or aromatic polyisocyanates on the other, as well as their precursors (polyisocyanates, polyols, prepolymers).

15. Polyamides and copolyamides which are derived from diamines and dicarboxylic acids and/or from aminocarboxylic acids or the corresponding lactams, such as polyamide 4, polyamide 6, polyamide 66, polyamide 610, polamide 11, polyamide 12, poly-2,4,4-trimethylhexamethyleneterephthalamide, poly-m-phenyleneisophthalamide, and their copolymers with polyethers, e.g. with polyethylene glycol, polypropylene glycol or polytetramethylene glycol.

16. Polyureas, polyimides and polyamide imides.

17. Polyesters which are derived from dicarboxylic acids and diols and/or from hydroxycarboxylic acids or the corresponding lactones, e.g. polyethylene terephthalate, polybutylene terephthalate, poly-1,4-dimethylolcyclohexane terephthalate, poly-[2,2-bis(4-hydroxyphenyl)propane]terephthalate, polyhydroxybenzoates, and also block polyether esters which are derived from polyethers having hydroxyl end groups, dialcohols and dicarboxylic acids.

18. Polycarbonates.

19. Polysulfones and polyether sulfones.

20. Crosslinked polymers which are derived from aldehydes on the one hand and from phenols, ureas and melamines on the other hand, such as phenol/formaldehyde resins, urea/formaldehyde resins and melamine/formaldehyde resins.

21. Unsaturated polyester resins which are derived from copolyesters of saturated and unsaturated dicarboxylic acids with polyhydric alcohols and vinyl compounds as crosslinking agents, and also their halogen-containing modifications of low combustibility.

22. Crosslinkable acrylic resins which are derived from substituted acrylic esters, e.g. from epoxy acrylates, urethane acrylates or polyester acrylates.

23. Alkyd resins, polyester resins and acrylate resins which are crosslinked with melamine resins, urea resins, poyisocyanates or epoxy resins.

24. Crosslinked epoxy resins which are derived from polyepoxides, e.g. bis-glycidyl ethers, or from cycloaliphatic diepoxides.

25. Naturally occurring polymers, such as cellulose, natural rubber and gelatin, and also chemically modified homologous derivatives thereof, such as cellulose acetates, cellulose propionates and cellulose butyrates, and cellulose ethers such as methylcellulose.

The stabilisation of surface-coating resins such as alkyd, acrylic and polyester resins, is of particular importance, especially when used as binders for acid-catalysed stoving lacquers.

The stabilisers of the invention are incorporated in the polymers in a concentration of 0.01 to 4% by weight, based on the material to be stabilised. Preferably 0.1 to 2% by weight of the compounds, based on the material to be stabilised, is incorporated thereinto.

Incorporation can be effected before, during or after the polymerisation, for example by blending the compounds and, if desired, further ingredients, into the melt by methods conventionally employed in the art, before or after the manufacture of shaped articles made therefrom. Incorporation in lacquers is preferably made to the solution of the lacquer before application of the lacquer.

The stabilisers can also be added in the form of a masterbatch which contains these compounds, for example in a concentration of 2.5 to 25% by weight, to the polymers which it is desired to stabilise.

In addition to the compounds of formula I, it is also possible to add further known stabilisers to the polymers.

1. ANTIOXIDANTS

1.1 Alkylated monophenols 2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-dicyclopentyl-4-methylphenol
2-(α-methylcyclohexyl)-4,6-dimethylphenol
2,6-di-octadecyl-4-methylphenol
2,4,6-tricyclohexylphenol
2,6-di-tert-butyl-4-methoxymethylphenol

1.2. Alkylated hydroquinones 2,6-di-tert-butyl-4-methoxyphenol
2,5-di-tert-butyl-hydroquinone
2,5-di-tert-amyl-hydroquinone
2,6-diphenyl-4-octadecyloxyphenol

1.3. Hydroxylated thiodiphenyl ethers 2,2'-thio-bis-(6-tert-butyl-4-methylphenol)
2,2-thio-bis-(4-octylphenol)
4,4'-thio-bis-(6-tert-butyl-3-methylphenol)
4,4'-thio-bis-(6-tert-butyl-2-methylphenol)

1.4. Alkyliden-bisphenols 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonlyphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
4,4'-methylene-bis-(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol-bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methylbenzyl)-6-tert-butyl-4-methylphenyl]-terephthalate.

1.5. Benzylcompounds 1,3,5-tri-(3,5-di-tert-butyl-4-hydroxybenzyl)-2,4,6-trimethylbenzene-di-(3,5-di-tert-butyl-4-hydroxybenzyl)-sulfide
isooctyl 3,5-di-tert-butyl-4-hydroxybenzyl-mercaptoacetate
bis-(4-tert-butyl-3-hydroxy-2,6-dimethylbenzyl)dithiol-terephthalate
1,3,5-tris-(3,5-di-tert-butyl-4-hydroxybenzyl)-isocyanurate
1,3,5-tris-(4-tert-butyl-3-hydroxy-2,6-dimethylbenzyl)-isocyanurate
dioctadecyl 3,5-di-tert-butyl-4-hydroxybenzylphosphonate
calcium-salt of monoethyl 3,5-di-tert-butyl-4-hydroxybenzylphosphonate

1.6. Acylaminophenols 4-hydroxylauric acid anilide
4-hydroxystearic acid anilide
2,4-bis-octylmercapto-6-(3,5-tert-butyl-4-hydroxyanilino)-s-triazine.

1.7. Esters of β-(3,5-di-tert-butyl-4-hydroxyphenyl)-propionic acid with monohydric or polyhydric alcohols, for example, with methanol, otadecanol, 1,6-hexanediol, neopentyl glycol, thiodiethylene glycol, diethylene glycol, triethylene glycol, pentaerythritol, trishydroxyethyl isocyanurate, dihydroxyethyloxalamide.

1.8. Esters of β-(5-tert-butyl-4-hydroxy-3-methylphenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, tris-hydroxyethyl isocyanurate or dihydroxyethyloxalamide.

1.9. Amides of β-(3,5-di-tert.butyl-4-hydroxyphenyl)propionic acid for example,
N,N'-di-(3,5-di-tert-butyl-4-hydroxyphenylpropionyl)-hexamethylendiamine
N,N'-di-(3,5-di-tert-butyl-4-hydroxyphenylpropionyl)-trimethylendiamine
N,N'-di-(3,5-di-tert-butyl-4-hydroxyphenylpropionyl)-hydrazine

2. UV ABSORBERS AND LIGHT STABILISERS 2.1. 2-(2'-Hydroxyphenyl)-benztriazoles, for exampe, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy-, 3', 5'-di-tert-amyl derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of substituted and unsubstituted benzoic acids, for example, phenyl salicylate, 4-tert.butyl-phenylsalicilate, octylphenyl salicylate, dibenzoylresorcinol, bis-(4-tert. butylbenzoyl)-resorcinol, benzoyl-resorcinol, 3,5-di-tert.-butyl-4-hydroxybenzoic acid 2,4-di-tert.butyl-phenyl ester and 3,5-di-tert.-butyl-4-hydroxybenzoate.

2.4. Acrylates, for example ethyl α-cyano-β,β-diphenylacrylate, methyl 2-carbomethoxycinnamate, methyl α-cyano-β-methyl-p-methoxycinnamate, butyl α-cyano-β-methyl-p-methoxy-cinnamate, methyl α-carbomethoxy-p-methoxy-cinnamate and N-(β-carbomethoxy-β-cyanovinyl)-2-methyl-indoline.

2.5 Nickel compounds, for example, nickel complexes of 2,2'-thiobis-[4-(1,1,3,3-tetramethylbutyl)-phenol], such as the 1:1 or 1:2 complex, with or without additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, e.g. of the methyl, ethyl or butyl ester, nickel complexes of ketoximes, e.g. of 2-hydroxy-4-methylphenyl undecyl ketoneoxime, nickel complexes of 1-phenyl-4-lauroyl-5-hydroxypyrazole, with or without additional ligands.

2.6. Oxalic acid diamides, for example, 4,4'-dioctyloxy-oxanilide, 2,2'-dioctyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert.butyloxanilide and mixtures of ortho-and para-methoxy- disubstituted and mixtures of o- and p-ethoxy-disubstituted oxanilides.

3. Metal deactivators, for example N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example triphenyl phosphite, diphenylalkyl phosphites, phenyldialkyl phosphites, tri(nonylphenyl) phosphite, trilauryl phosphite, trioctadecyl phosphite, distearylpentaerythritol diphosphite, tris-(2,4-di-tert-butylphenyl) phosphite, diisodecylpentaerythritol diphosphite, di-(2,4-di-tert-butylphenyl)pentaerythritol diphosphite, tristearylsorbitol triphosphite, tetrakis-(2,4-di-tert.butylphenyl)-4,4'-biphenylene diphosphite.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zincdibutyldithiocarbamate, dioctadecyldisulfide, pentaerythritoltetrakis-(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamids, polyurethanes, alkali metal salts and alkaline earth metal salts of higher fatty acids for example calcium stearate zinc stearate, manganese stearate, sodium ricinoleate and potassium palmitate, antimony pyrocatechoate or tin pyrocatechoate.

8. Nucleating agents, for example, 4-tert-butylbenzoic acid, adipic acid, diphenylacetic acid.

When known stabilisers are used concurrently, synergistic effects can be obtained. This frequently happens whenever other light stabilisers or organic phosphites are used concurrently. The concurrent use of antioxidants for stabilising polyolefins is of particular importance. Further, other additives conventionally employed in plastics technology can also be added, e.g. flame retardants, antistatic agents, plasticisers, lubricants, blowing agents, pigments or fillers.

Accordingly, the invention also relates to the organic polymers stabilised by the addition of 0.1 to 4% by weight of a compound of the formula I, which polymers, if desired, can also contain other known and customary additives. The stabilised plastics can be used in very diverse forms, for example as films fibres, ribbons or profiles, and especially as binders for lacquers.

The following Examples describe the preparation and use of the compounds of the invention in more detail. Parts and percentages are by weight.

EXAMPLE 1

0.4 ml of tetrabutyl orthotitanate is stirred into a hot (125° C.) solution of 17.4 g (0.06 mole) of tetramethyl butane-1,2,3,4-tetracarboxylate (m.p. 73°–76° C.) and 47.8 g (0.24 mole) of 1-acetyl-4-hydroxy-2,2,6,6-tetramethylpiperidine (m.p. 128°–129° C.) in 400 ml of anhydrous xylene. In a constant weak stream of nitrogen, the methanol split off during the reaction is continuously distilled off from the reaction mixture through a descending cooler. The temperature of the reaction mixture is slowly raised over 3 hours to about 135°–140° C. and kept for 2 hours, while distilling off further methanol and a small amount of xylene. The temperature is then raised to about 150° C. and kept for 5 hours. For purification, the crude product, which gradually congeals to a crystalline solid on cooling, is dissolved in 500 ml of acetonitrile. The solution is clarified hot with 2 g of diatomaceous earth and 2 g of activated carbon, filtered and the filtrate is cooled. The crystallised tetra-(1-acetyl-2,2,6,6-tetramethyl-4-piperidyl) butane-1,2,3,4-carboxylate is isolated by filtration and dried in vacuo. The product melts at 185°–186° C. and the $^1$H-NMR spectrum is in accord with the indicated structural formula (compound 1).

| $C_{52}H_{86}N_4O_{12}$ | cal. | C 65.11 | H 9.04 | N 5.84% |
|---|---|---|---|---|
| (959.22) | found | C 65.3 | H 8.9 | N 5.9% |

EXAMPLE 2

In corresponding manner, transesterification of 1 equivalent of tetramethyl butane-1,2,3,4-tetracarboxylate with 4 equivalents of 1-acryloyl-4-hydroxy-2,2,6,6-tetramethylpiperidine (in the presence of 0.1% of di-tert-butyl-p-cresol and 0.1% of hydroquinone monomethyl ether) affords tetra-(1-acryloyl-2,2,6,6-tetramethyl-4-piperidyl) butane-1,2,3,4-tetracarboxylate (compound 2) with a melting point of 154°–155° C.

| $C_{56}H_{86}N_4O_{12}$ | cal. | C 66.7 | H 8.61 | N 5.56% |
|---|---|---|---|---|
| (1007.3) | found | C 66.9 | H 8.7 | N 5.5% |

EXAMPLE 3

Following the procedure of Example 1, transesterification of 1 equivalent of tetramethyl propane-1,1,2,3- tetracarboxylate with 4 equivalents of 4-hydroxy-2,2,6,6-tetramethylpiperidine in the presence of tetrabutyl titanate as catalyst affords tetra-(2,2,6,6-tetramethyl-4-piperidyl)titanate with a melting point of 91°–93° C. 10 g of this compound are treated with 35 g of acetic anhydride for 20 hours at 105° C. The mixture is concentrated in vacuo, leaving as residue 12 g of tetra-(1-acetyl-2,2,6,6-tetramethyl-4-piperidyl) propane-1,1,2,3-tetracarboxylate as a yellow viscous oil which becomes amorphous at low temperature and softens at about 50° C. (compound 3).

| | | | | |
|---|---|---|---|---|
| $C_{51}H_{84}N_4O_{12}$ | cal. | C 64.8 | H 8.96 | N 5.9% |
| (945.2) | found | C 64.6 | H 9.10 | N 5.8% |

The $^1$H-NMR spectrum is in accord with the indicated structural formula.

EXAMPLE 4

Stabilisation of polypropylene sheets 100 parts of polypropylene powder (Moplen, fibre grade, manufactured by Montedison), 0.2 part of β-(3,5-di-tert-butyl-4-hydroxyphenyl)-propionic acid octadecyl ester, 0.1 part of calcium stearate and 0.25 part of a stabiliser of Table 1 are homogenised in a Brabender plastograph for 10 minutes at 200° C. The resultant plastic mass is removed from the kneader as quickly as possible and pressed to a 2–3 mm sheet in a toggle press. A portion of the sheet is cut out and pressed between two ultra-gloss rigid aluminum sheets with a hand-operated hydraulic laboratory press for 6 minutes at 260° C. to a 0.1 mm sheet, which is immediately chilled in cold water. Segments are then punched out of this sheet and exposed in the xenotest 1200. These samples are taken out of the exposure apparatus at regular intervals and examined for their carbonyl content in an IR spectrophotometer. The increase in the carbonyl extinction at 5.85μ during exposure is a reference value for the degradation of the polymer by photooxidation [see L. Balaban et al., J. Polymer Sci., Part C; 22, 1059–1071 (1969)] and, as experience shows, is associated with a decrease in the mechanical properties of the polymer. The time taken until a carbonyl extinction of about 0.3 is reached, at which value the comparison sheet is brittle, serves as an indication of the protective action. To test the volatility and water extractability, (a) some of the samples are heated, before exposure, for 7 days in a forced draught oven to 120° C. and (b) other samples are treated, before exposure, for 7 days with water of 90° C.

The results with and without pretreatment of the samples are reported in Table 1.

TABLE 1

| Stabiliser Compound No. | Exposure time until a carbonyl extinction of 0.3 (in hours) | | |
|---|---|---|---|
| | without pretreatment | 7 days at 120° | water extraction for 7 days at 90° C. |
| without | 1100 | 290 | 310 |
| 1 | 5080 | 7620 | 480 |
| 2 | 4500 | 4780 | 960 |
| 3 | >5180 | 5010 | 1180 |

What is claimed is:
1. A compound of the formula I

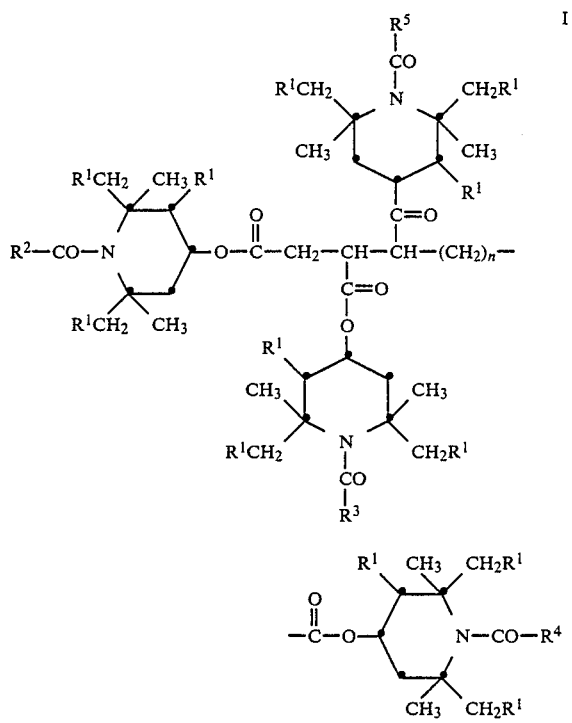

wherein n is 0 or 1, $R^1$ is hydrogen or $C_1$–$C_4$alkyl, and $R^2$, $R^3$, $R^4$ and $R^5$ are each independently hydrogen, $C_1$–$C_{17}$alkyl, $C_2$–$C_{17}$alkenyl, $C_5$–$C_8$cycloalkyl, $C_5$–$C_8$cycloalkylalkyl or $C_5$–$C_8$alkylcycloalkyl, $C_6$–$C_{10}$aryl, $C_7$–$C_{16}$alkylphenyl, $C_7$–$C_{12}$aralkyl or $C_8$–$C_{18}$alkylphenylalkyl.

2. A compound according to claim 1 of the formula I, wherein $R^1$ is hydrogen.

3. A compound according to claim 1 of the formula I, wherein $R^2$, $R^3$, $R^4$ and $R^5$ are identical and are $C_1$–$C_5$alkyl or $C_2$–$C_5$alkenyl.

4. A compound according to claim 3, wherein $R^2$, $R^3$, $R^4$ and $R^5$ are methyl or vinyl.

5. An organic polymer which is stabilised against photochemical degradation and which contains 0.1 to 4% by weight of a compound of the formula I.

6. An organic polymer which is stabilised according to claim 5 as binder for lacquers, especially for acid-catalysed stoving lacquers.

* * * * *